(12) United States Patent
Warnock et al.

(10) Patent No.: US 8,362,088 B2
(45) Date of Patent: Jan. 29, 2013

(54) METHOD AND ARTICLE OF MANUFACTURE FOR ENCAPSULATING A HOMEOPATHIC INGREDIENT WITH A SECOND INGREDIENT

(76) Inventors: W. Matthew Warnock, Sandy, UT (US); Shane Hinze, Omaha, NE (US)

( * ) Notice: Subject to any disclaimer, the term of this patent is extended or adjusted under 35 U.S.C. 154(b) by 477 days.

(21) Appl. No.: 11/956,019

(22) Filed: Dec. 13, 2007

(65) Prior Publication Data

US 2008/0146677 A1 Jun. 19, 2008

Related U.S. Application Data

(60) Provisional application No. 60/874,732, filed on Dec. 14, 2006.

(51) Int. Cl.
*A61K 47/26* (2006.01)
*A61K 47/12* (2006.01)
*A61K 47/04* (2006.01)

(52) U.S. Cl. ........ 514/770; 514/769; 514/777; 514/778; 514/781; 514/784; 514/785

(58) Field of Classification Search ....................... None
See application file for complete search history.

(56) References Cited

U.S. PATENT DOCUMENTS

| | | | | |
|---|---|---|---|---|
| 6,045,825 | A * | 4/2000 | Cody | 424/451 |
| 6,248,307 | B1 * | 6/2001 | Borneman et al. | 424/451 |
| 6,328,994 | B1 * | 12/2001 | Shimizu et al. | 424/489 |
| 7,128,932 | B2 * | 10/2006 | Bombardelli et al. | 424/739 |
| 2002/0146456 | A1 * | 10/2002 | Ramstack et al. | 424/489 |
| 2004/0247649 | A1 * | 12/2004 | Pearce et al. | 424/440 |
| 2006/0134202 | A1 * | 6/2006 | Hack et al. | 424/464 |

FOREIGN PATENT DOCUMENTS

| | | | |
|---|---|---|---|
| EP | 0687466 | * | 6/1995 |
| JP | 59071673 | * | 4/1984 |

OTHER PUBLICATIONS

Demchenko 2008. Introduction to Fluorescence Sensing. Theoretical Aspects, pp. 37-64.*
Barrett 2004. The Handbooks of Clinically Tested Herbal Remedies. Chapter 5. The Importance and Difficulty in Determining the Bioavailability of Herbal Preparations. pp. 49-58.*
Gaedcke et al, 2003. Herbal Medicinal Products. Chapter 1. Definitions.pp. 1-29.*
Ansel et al, 1999. Pharmaceutical Dosage Forms and Drug Delivery Systems, Seventh edition, pp. 87-92.*

* cited by examiner

*Primary Examiner* — Suzanne Ziska

(74) *Attorney, Agent, or Firm* — Kunzler Law Group, PC

(57) ABSTRACT

An apparatus, system, and method are disclosed for encapsulating a homeopathic ingredient with a second ingredient. A homeopathic carrier is prepared by applying the homeopathic ingredient to at least one element. The element is selected from the second ingredient, an excipient, and a capsule assembly. The second ingredient is encapsulated in a closed capsule assembly. The closed capsule assembly comprises the homeopathic carrier.

18 Claims, 7 Drawing Sheets

METHOD AND ARTICLE OF MANUFACTURE FOR ENCAPSULATING A HOMEOPATHIC INGREDIENT WITH A SECOND INGREDIENT

CROSS-REFERENCES TO RELATED APPLICATIONS

This application is a continuation-in-part of and claims priority to U.S. Provisional Patent Application No. 60/874,732 entitled "METHOD FOR INCORPORATING HOMEOPATHIC MEDICINES INTO HERBAL MEDICINES OR OTHER DIETARY SUPPLEMENTS" and filed on Dec. 14, 2006 for W. Matthew Warnock and Shane Hinze, which is incorporated herein by reference.

BACKGROUND OF THE INVENTION

1. Field of the Invention

This invention relates to encapsulating homeopathic ingredients and more particularly relates to encapsulating a homeopathic ingredient with a second ingredient.

2. Description of the Related Art

Herbal medicines, medicinal substances, and other dietary supplements may be taken orally to promote increased physical health. Herbal medicines, medicinal substances, and dietary supplements are referred to herein as ingredients. For example, a person may ingest an herb containing compounds that reduce blood pressure. Powdered herbs are often bulky, requiring large capsules or tablets to contain an effective dose.

Similarly, homeopathic remedies are often taken orally. For example, a homeopathic ingredient may be taken to strengthen the body's mechanisms for regulating blood pressure. Homeopathic remedies are prepared by repeated dilution and succussion of a homeopathic ingredient with a diluent such as water, alcohol, or lactose. The diluted homeopathic ingredient may then optionally be applied to a homeopathic carrier for administration. The homeopathic carrier allows the homeopathic ingredient to be taken orally in a more convenient form.

It is not always easy to combine a homeopathic ingredient with another ingredient. For example, a water-based homeopathic ingredient may promote bacterial growth if the homeopathic ingredient is combined with an herb. In addition, a homeopathic ingredient in solid form may take up capsule space that may be needed for bulky herbal ingredients.

SUMMARY OF THE INVENTION

From the foregoing discussion, there is a need for a method and article of manufacture that encapsulates a homeopathic ingredient with a second ingredient. Beneficially, such a method and article of manufacture would allow the second ingredient and the homeopathic ingredient to be combined in a single convenient capsule. In addition, the method and article may maximize the amount of capsule space available for other ingredients such as herbal ingredients.

The present invention has been developed in response to the present state of the art, and in particular, in response to the problems and needs in the art that have not yet been fully solved by currently available homeopathic ingredient packaging methods. Accordingly, the present invention has been developed to provide a method and article of manufacture for encapsulating a homeopathic ingredient with a second ingredient that overcome many or all of the above-discussed shortcomings in the art.

A method of the present invention is presented for encapsulating a homeopathic ingredient with a second ingredient. A homeopathic carrier is prepared by applying the homeopathic ingredient to at least one element. The element is selected from the second ingredient, an excipient, and a capsule assembly. The second ingredient is encapsulated in a closed capsule assembly. The closed capsule assembly comprises the homeopathic carrier.

An article of manufacture of the present invention is also presented for encapsulating a homeopathic ingredient with a second ingredient. The article includes a homeopathic carrier comprising the homeopathic ingredient applied to at least one element selected from the second ingredient, an excipient, and a capsule assembly. The second ingredient is encapsulated in a closed capsule assembly. The closed capsule assembly comprises the homeopathic carrier.

References throughout this specification to features, advantages, or similar language do not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

The present invention encapsulates a homeopathic ingredient with a second ingredient. The present invention allows the second ingredient to be combined with the homeopathic ingredient without sacrificing space in the capsule and may facilitate the encapsulation of the second ingredient. These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE INVENTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagram that follows is set forth as a logical flow chart diagram. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. For instance, steps may occur concurrently. Additionally, the order in which a particular method occurs may or may not strictly adhere to the order of the corresponding steps shown.

Figure 1:
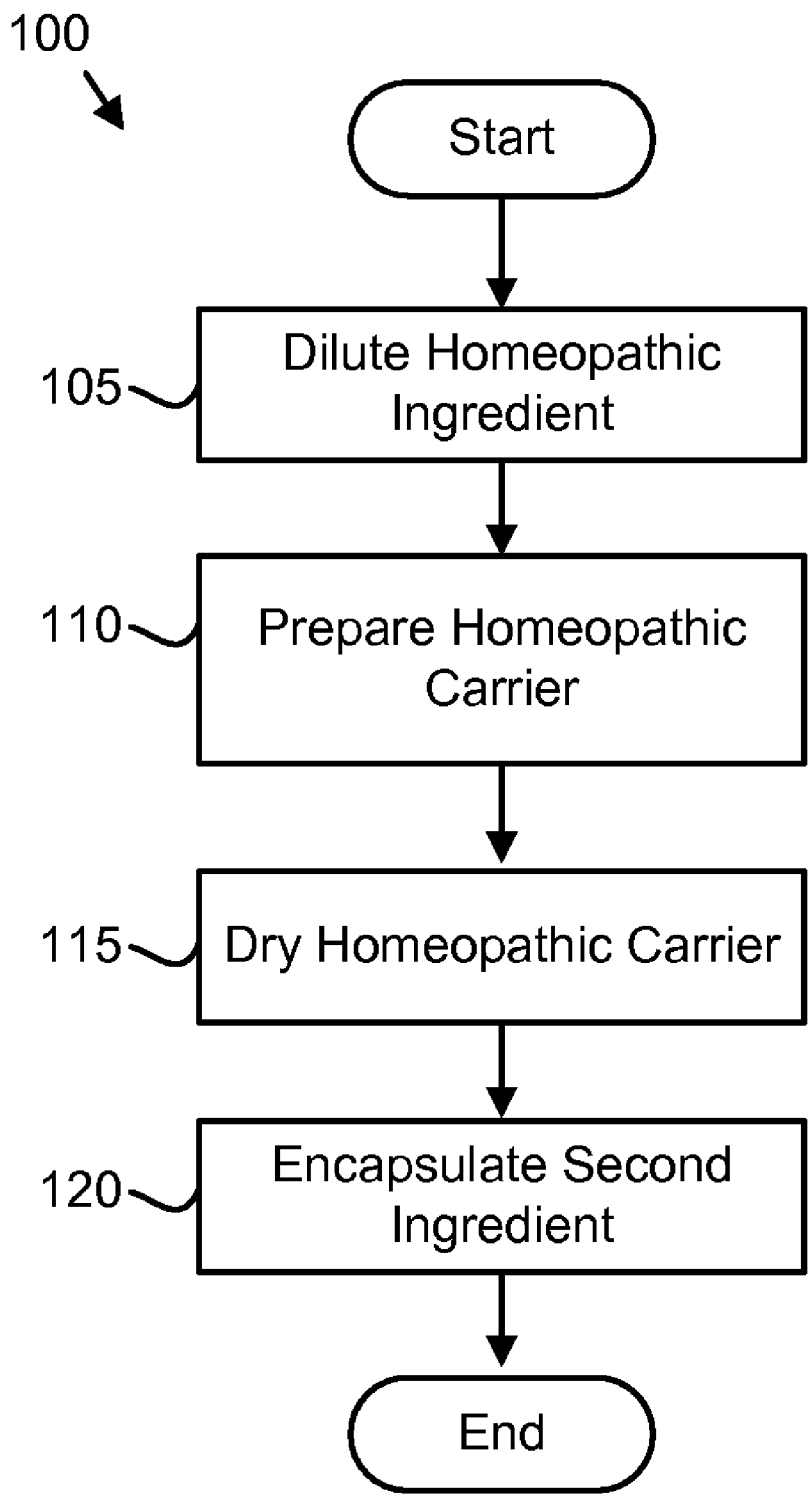
FIG. 1 is a schematic flow chart diagram illustrating one embodiment of an encapsulation method of the present invention.
Figure 2A:
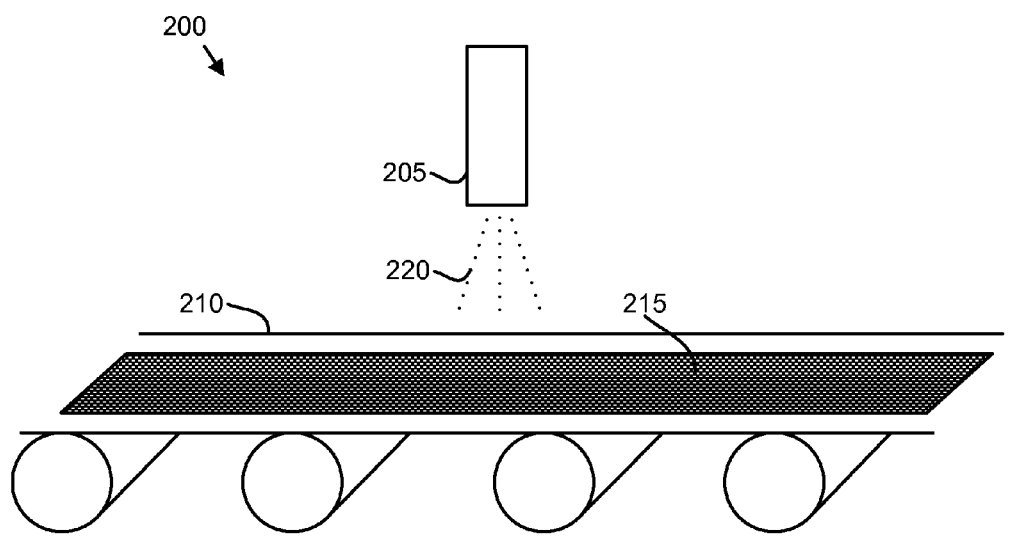
FIG. 2A is a perspective drawing illustrating one embodiment of an application device of the present invention.
Figure 2B:
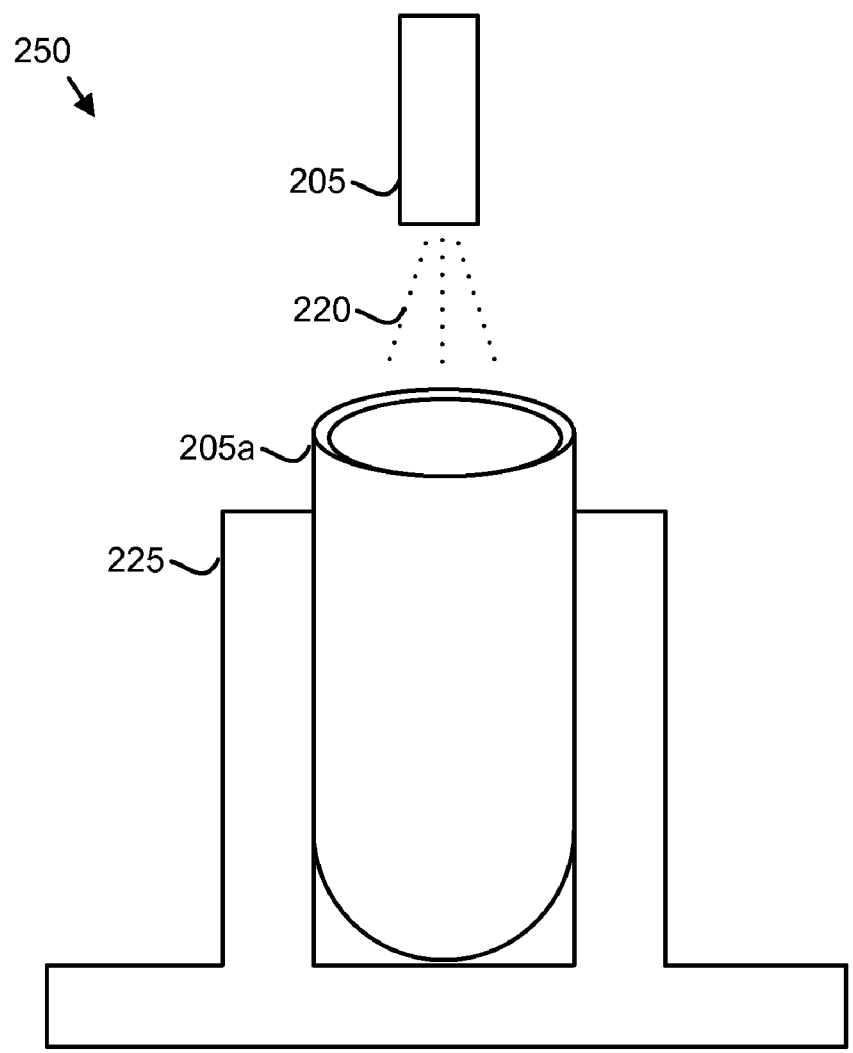
FIG. 2B is a perspective drawing illustrating one alternate embodiment of an application device of the present invention.
Figure 2C:
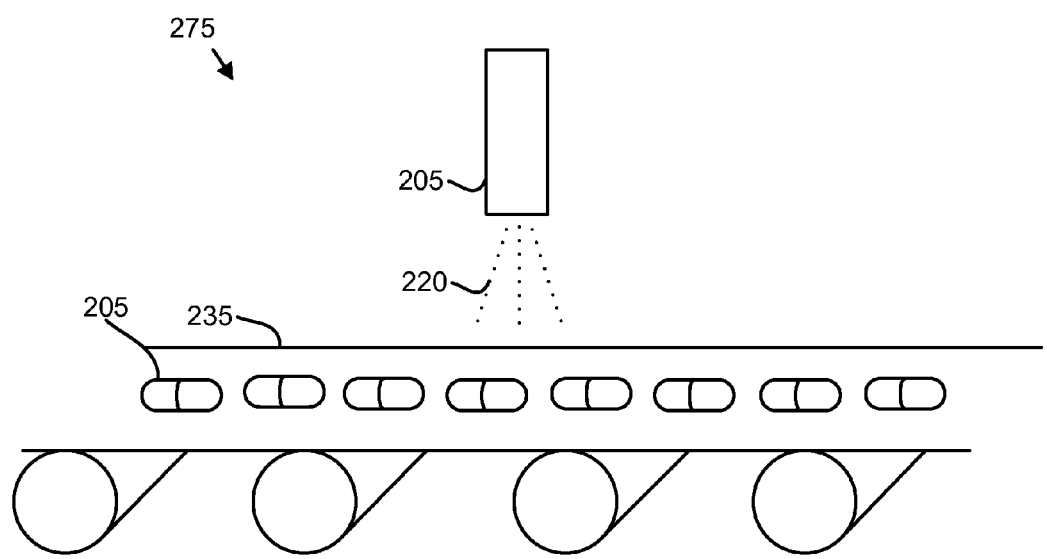
FIG. 2C is a perspective drawing illustrating one embodiment of a capsule application device of the present invention.
Figure 3:
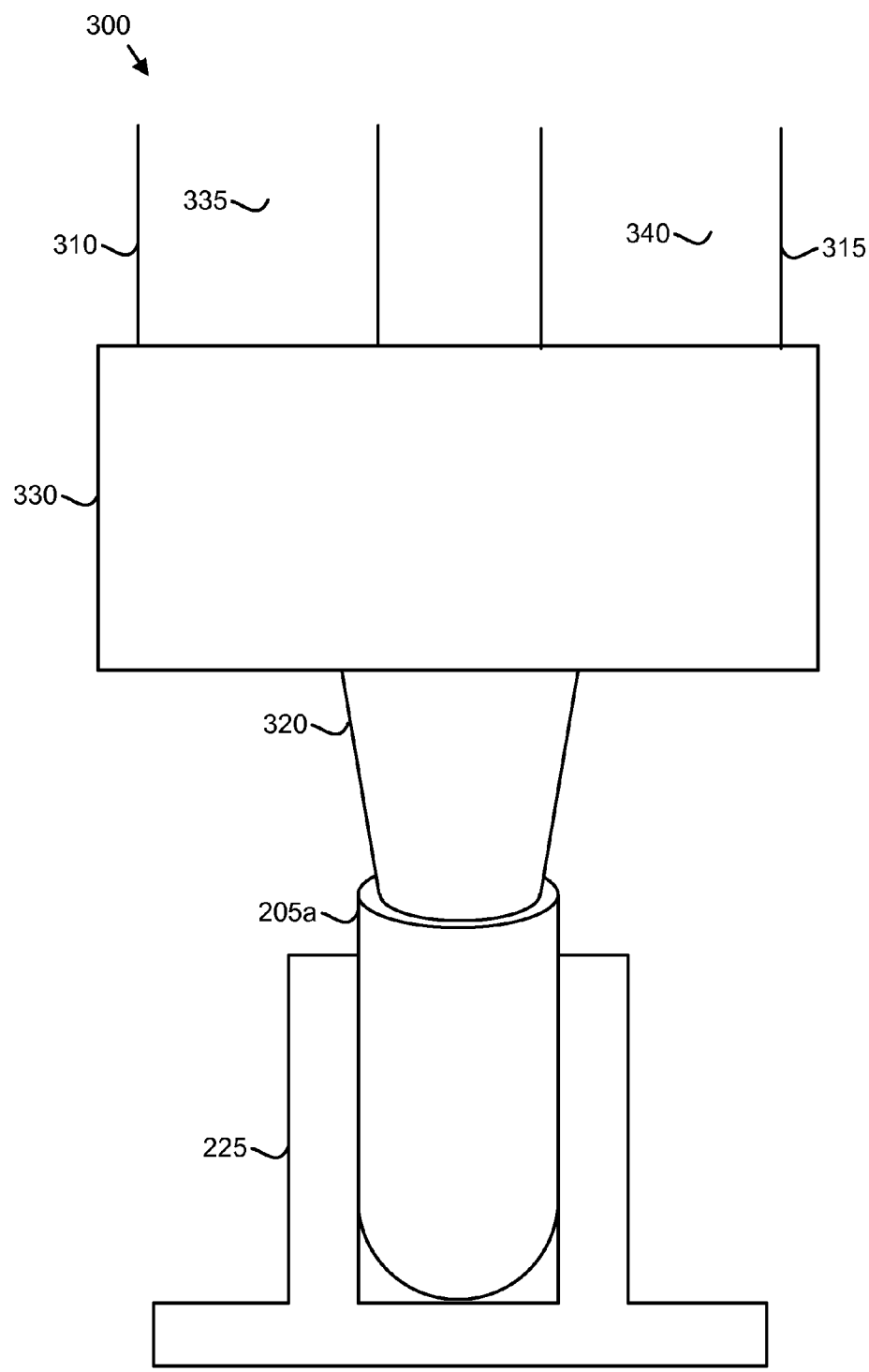
FIG. 3 is a perspective drawing illustrating one embodiment of an encapsulation device of the present invention.
Figure 4:
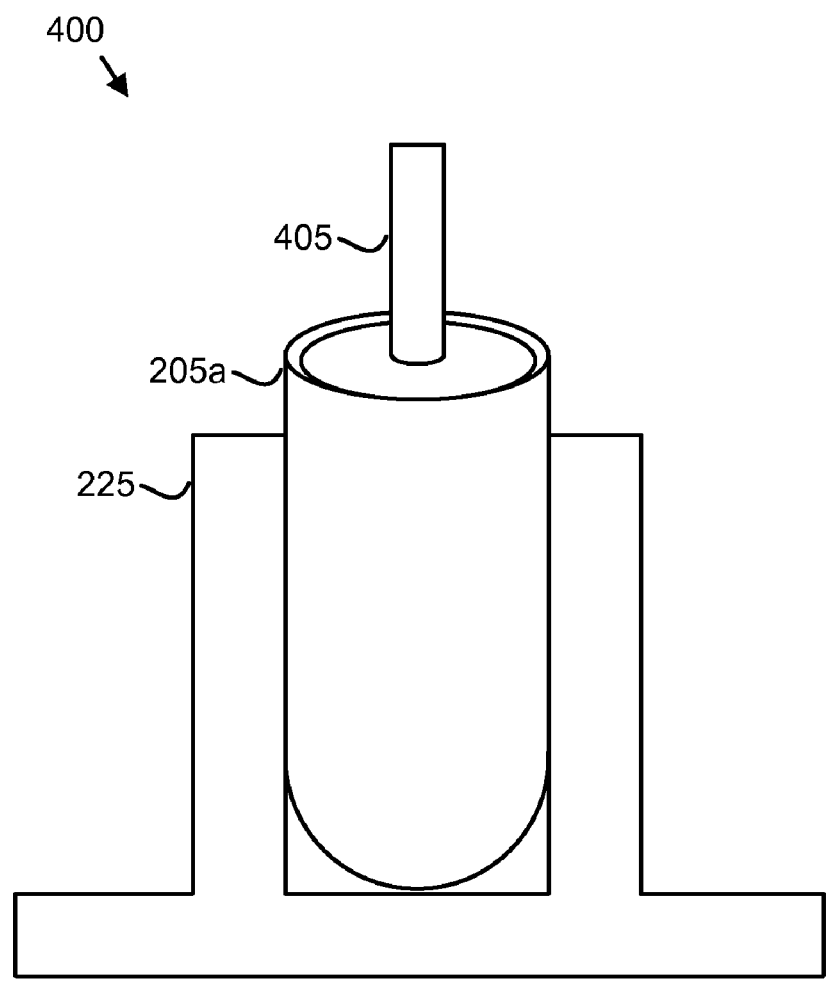
FIG. 4 is a perspective drawing illustrating one embodiment of a tamping device in accordance with the present invention.
Figure 5:
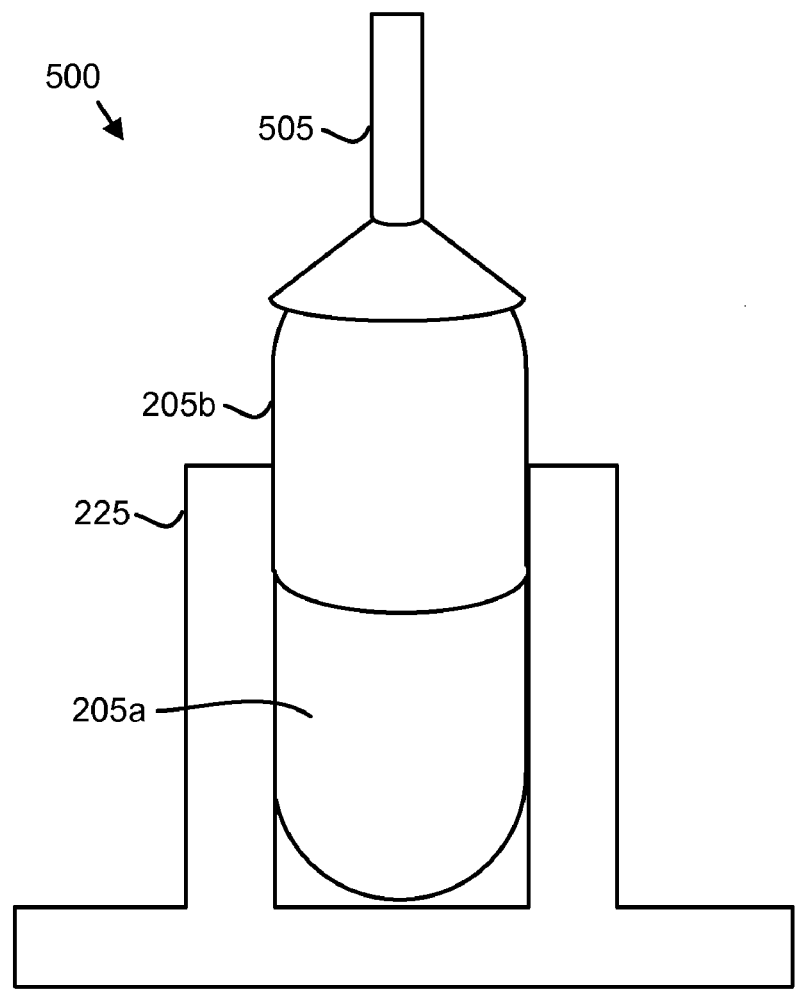
FIG. 5 is a perspective drawing illustrating one embodiment of a closing device in accordance with the present invention.

FIG. 1 is a schematic flow chart diagram illustrating one embodiment of an encapsulation method 100 of the present invention. The method 100 may be practiced as part of a manufacturing process for a homeopathic ingredient.

The method 100 starts and dilutes 105 a homeopathic ingredient with a diluent. In one embodiment, the diluent is a liquid diluent. The diluent may be purified water, strong alcohol, or glycerin. The homeopathic ingredient may be mixed with the liquid diluent. In an alternate embodiment, the diluent may be a solid such as lactose. After each dilution, the ingredient is succussed in accordance with homeopathic practice.

In one embodiment, the homeopathic ingredient is diluted 105 to a potency in the range of 2 C to 30 C. A dilution of nC as used herein refers to diluting one part of the homeopathic ingredient with 100 parts of the diluent and succussing the dilution as is well known to those of skill in the art, wherein the dilution/succussion process is repeated n times. For example, if the homeopathic ingredient is diluted with 100 parts of diluent and succussed, repeated five times, the dilution has a potency of 5 C.

In an alternate embodiment, the homeopathic ingredient is diluted 105 to a potency in the range of 2× to 30×. As used herein, a dilution of nX refers to diluting one part of the homeopathic ingredient with ten parts of the diluent and then succussing the dilution, wherein the combination of dilution and succession steps are repeated n times. For example, if the homeopathic ingredient is diluted with ten parts of diluent and succussed, repeated 20 times, the dilution has a potency of 20×.

An element is prepared 110 as a homeopathic carrier. The homeopathic carrier allows the homeopathic ingredient to be ingested. The homeopathic ingredient may be applied to the element to prepare the element as a homeopathic carrier. In a certain embodiment, the dilution of the homeopathic ingredient may be applied to the element.

In one embodiment, the element is a second ingredient. The second ingredient may comprise a botanical substance. Alternatively, the second ingredient may comprise a zoological substance. In a certain embodiment, the second ingredient comprises a mineral. One of skill in the art will recognize that the second ingredient may comprise a plurality of substances combined in various ratios.

Alternatively, the element may be an excipient. The excipient may have good compressibility, be highly dilutive, have a low coefficient of friction, and have good flowability. The compressibility may be in the range of twenty to thirty percent (20% to 30%). In one embodiment, the kinetic coefficient of friction of the excipient is in the range of zero point twenty five to zero point eighty five at thirty degrees Celsius (0.25 to 0.85 at 30° C.). In a certain embodiment, the kinetic coefficient of friction of the excipient is in the range of zero point thirty five to zero point sixty at thirty degrees Celsius (0.35 to 0.60 at 30° C.). The flowability index may be in the range of seventy five to ninety five (75 to 95), with an angle of repose in the range of fifteen to forty degrees (15 to 40°) and an angle of spatula in the range of twenty five to fifty five degrees (25 to 55°). In a certain embodiment, the flowability index is in the range of eighty to ninety (80 to 90), the angle of repose is in the range of twenty four to thirty two degrees (24 to 32°), and the angle of spatula is in the range of thirty five to forty five degrees (35 to 45°).

In one embodiment, the excipient comprises microcrystalline cellulose. Alternatively, the excipient may comprise magnesium stearate, stearic acid, and/or silicon dioxide. In one embodiment, the excipient may be comprised of a plurality of substances. For example, the excipient may comprise both microcrystalline cellulose and silicon dioxide.

In an alternate embodiment, the excipient comprises at least one of an antiadherent, a filler, a diluent, a disintegrant, a glidant, a lubricant, a preservative, a binder, a coating, and a sorbent. The filler may comprise at least one of calcium phosphate, sucrose, glucose, mannitol, sorbitol, calcium carbonate, and vegetable stearin. The lubricant may comprise at least one of talc, silica, and vegetable stearin.

The excipient may be a third ingredient. In one embodiment, the excipient is a botanical substance. Alternatively, the excipient may be a zoological substance and/or a mineral. In one embodiment, the excipient comprises a plurality of supplements.

In one embodiment, an excipient further dilutes the homeopathic ingredient. For example, one part of the homeopathic ingredient may be mixed with one thousand (1000) parts of the excipient to dilute the homeopathic ingredient.

In a certain embodiment, the element is a capsule assembly. For example, the homeopathic ingredient may be applied to a surface of the capsule assembly as will be described hereafter.

The homeopathic carrier may be dried 115 if the homeopathic ingredient is diluted with a liquid diluent. In one embodiment, the homeopathic carrier is placed within an oven for a specified time interval. Alternatively, a shallow layer of the homeopathic carrier, such as the excipient and/or second ingredient with applied homeopathic ingredient, may be exposed to the air for a specified time interval. In one embodiment, the homeopathic carrier is tested to assure sufficient drying.

The second ingredient is encapsulated 120 in a closed capsule assembly. In one embodiment, the excipient acts as a flow agent and carries the second ingredient into the capsule. In one embodiment, a low kinetic coefficient of friction for the excipient prevents the second ingredient and excipient from clumping and/or sticking while flowing into the capsule. Thus a controlled, repeatable quantity of excipient and second ingredient may be added to each capsule. The encapsulation will be described hereafter in greater detail.

FIG. 2A is a perspective drawing illustrating one embodiment of an application device 200 of the present invention. The device 200 includes a dispenser 205, a conveyor belt 210, the excipient and/or second ingredient 215, and a dilution 220. The dilution 220 is the dilution of the homeopathic ingredient with the diluent. The device 200 may prepare 110 at least one element selected from the second ingredient, the excipient, and the capsule assembly as a homeopathic carrier as described in step 110 of FIG. 1. In particular, the device 200 may be used to prepare the excipient and/or second ingredient 215 as the homeopathic carrier. The description of the device 200 refers to elements of FIG. 1, like numbers referring to like elements.

The conveyor belt 210 may carry the excipient and/or second ingredient 215 beneath the dispenser 205. In one embodiment, the excipient and/or second ingredient 215 is disposed with a specified density on the conveyor belt 210. The dispenser 205 may spray a metered amount of the dilution 220 onto the excipient and/or second ingredient 215. The conveyor belt 210 may carry the excipient and/or second ingredient 215 with dilution 220 to be dried. In one embodiment, the conveyor belt 210 carries the excipient and/or second ingredient 215 with applied dilution 220 through an oven, beneath heating lamps, or the like.

In an alternate embodiment, the excipient and/or second ingredient 215 may be disposed on a table in a solids processor and the dispenser 205 may apply the dilution 220 to the excipient and/or second ingredient 215 on the table. One of skill in the art will recognize that the dilution 220 may be applied to the excipient and/or second ingredient 215 using additional processes and techniques.

FIG. 2B is a perspective drawing illustrating one alternate embodiment of an application device 250 of the present invention. The device 250 applies the dilution of the homeopathic ingredient 220 to the capsule assembly. The description of the device 250 refers to elements of FIGS. 1-2A, like numbers referring to like elements.

In one embodiment, the capsule assembly includes a proximal capsule end 205*a* and a distal capsule end. The proximal capsule end 205*a* is shown disposed in a fixture 225. One of skill in the art will recognize that the invention may also be practiced with the distal capsule end disposed in the fixture.

The dispenser 205 may spray a metered amount of the dilution 220 onto the proximal capsule end 205*a*. In one embodiment, a plurality of fixtures 225 present a plurality of proximal capsule ends 205*a* to the dispenser 205 for application of the dilution 220. The proximal capsule end 205*a* may subsequently be dried using an oven, heat lamps, open air, or the like.

FIG. 2C is a perspective drawing illustrating one embodiment of a capsule application device 275 of the present invention. The device 275 applies the dilution of the homeopathic ingredient 220 to the closed capsule assembly 205. The description of the device 275 refers to elements of FIGS. 1-2B, like numbers referring to like elements.

The filled and closed capsule assembly 205 is arranged on a spray bed 235 and sprayed with the diluted homeopathic ingredient so as to make the closed capsule assembly 205 a homeopathic carrier. The closed capsule assembly 205 may further be dried before packaging.

FIG. 3 is a perspective drawing illustrating one embodiment of an encapsulation device 300 of the present invention. The device 300 may encapsulate 120 the second ingredient in the proximal capsule end 205*a* using the excipient and/or second ingredient 215 to carry the second ingredient into the proximal capsule end 205*a* as described in step 120 of FIG. 1. The description of the device 300 refers to elements of FIGS. 1-2C, like numbers referring to like elements.

A supplement feed line 310 carries the second ingredient 335 to a mixer 330. An excipient feed line 315 carries the excipient 340 to the mixer 330. The mixer 330 may uniformly combine the second ingredient 335 and excipient 340 in specified proportions. In one embodiment, the mixer 330 employees rotating blades to combine the second ingredient 335 and the excipient 340.

A nozzle 320 delivers the second ingredient 335 and the excipient 340 to the proximal capsule end 205*a*. The second ingredient 335 may be prone to clumping and/or prone to adhering to the nozzle 320 and/or mixer 330. Because of the low kinetic coefficient of friction and good flowability of the excipient 340, the excipient 340 may carry the second ingredient 335 through the nozzle 320 and into the proximal capsule end 205*a*.

The proximal capsule end 205*a* is held in place by a fixture 225. A plurality of fixtures 225 may move a plurality of capsules 205 beneath the nozzle 320. The nozzle 320 may fill each proximal capsule end 205*a* in turn.

FIG. 4 is a perspective drawing illustrating one embodiment of a tamping device 400 in accordance with the present invention. The tamping device 400 may settle the second ingredient 335 and the excipient 340 in the proximal capsule end 205*a* as part of encapsulating the second ingredient as described in step 120 of FIG. 1. The description of the device 400 refers to elements of FIGS. 1-3, like numbers referring to like elements.

A tamper 405 compacts the second ingredient 335 and the excipient 340 in the proximal capsule end 205*a*. The fixture 225 may hold the proximal capsule end 205*a* during tamping. In one embodiment, a plurality of fixtures 225 carry a plurality of capsules 205 in turn to the tamper 405.

FIG. 5 is a perspective drawing illustrating one embodiment of a closing device 500 in accordance with the present invention. The device 500 completes the encapsulation 120 of the second ingredient 335 and the excipient 340 of step 120 of FIG. 1. The description of the device 500 refers to elements of FIGS. 1-4, like numbers referring to like elements.

The proximal capsule end 205*a* is held in place by the fixture 225. An armature 505 fits a distal capsule end 205*b* to the proximal capsule end 205*a* to complete encapsulation of the capsule assembly as a closed capsule assembly. A plurality of fixtures 225 may position a plurality of proximal capsule ends 205*a* to receive the distal capsule end 205*b*.

The capsule ends 205 may be comprised of vegetarian cellulose. The closed capsule assembly may be ingested by a patient, providing the patient with the benefit of both the second ingredient 335 and the homeopathic ingredient. The present invention provides for the homeopathic ingredient and the second ingredient 335 to be encapsulated together using at least one of the second ingredient 335, excipient 340, and capsule assembly as the homeopathic carrier.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for encapsulating a homeopathic ingredient with a second ingredient, the method comprising:
preparing an excipient as a homeopathic carrier by diluting and succussing the homeopathic ingredient in a liquid diluent, applying the diluted homeopathic ingredient to the excipient, and drying the diluted homeopathic ingredient on the excipient; and
encapsulating the second ingredient using the excipient to carry the second ingredient into a capsule assembly, wherein the excipient is a glidant with a kinetic coefficient of friction in the range of 0.35 to 0.60, the second ingredient is therapeutic and non-homeopathic, and the capsule assembly comprises the homeopathic carrier.

2. The method of claim 1, wherein the excipient comprises microcrystalline cellulose.

3. The method of claim 1, wherein the excipient is selected from magnesium stearate, stearic acid, and silicon dioxide.

4. The method of claim 1, wherein the excipient has a flowability index in the range of 75-95.

5. The method of claim 4, wherein the excipient has a flowability index in the range of 80-90.

6. The method of claim 1, wherein the excipient is further selected from an antiadherent, a filler, a diluent, a disintegrant, a lubricant, a preservative, a binder, a coating, and a sorbent.

7. The method of claim 6, wherein the filler is selected from calcium phosphate, sucrose, glucose, mannitol, sorbitol, calcium carbonate, and vegetable stearin.

8. The method of claim 6, wherein the lubricant is selected from talc, silica, and vegetable stearin.

9. The method of claim 1, wherein the homeopathic ingredient is diluted with a liquid diluent selected from purified water, strong alcohol, dispensing alcohol, and glycerin to form the diluted homeopathic ingredient.

10. The method of claim 9, wherein the diluted homeopathic ingredient has a potency in the range of 2 C to 30 C, wherein a dilution of nC dilutes one part of the homeopathic ingredient with 100 parts of the diluent and is succussed, and the dilution/succussion process repeated n times.

11. The method of claim 10, wherein the diluted homeopathic ingredient has a potency in the range of 2× to 30×, wherein a dilution of nX dilutes one part of the homeopathic ingredient with ten parts of the diluent and is succussed, and the combination of dilution and succussion are repeated n times.

12. The method of claim 1, wherein the diluted homeopathic ingredient is sprayed onto the excipient.

13. The method of claim 1, wherein the excipient further dilutes the homeopathic ingredient.

14. The method of claim 1, wherein the second ingredient is selected from a botanical substance, a zoological substance, and a mineral.

15. The method of claim 1, wherein the homeopathic ingredient is applied to the closed capsule assembly.

16. An article of manufacture, the article comprising:
a capsule assembly;
a homeopathic carrier excipient prepared by diluting and succussing a homeopathic ingredient in a liquid diluent, applying the diluted homeopathic ingredient to the excipient, and drying the diluted homeopathic ingredient on the excipient, wherein the excipient is a glidant with a kinetic coefficient of friction in the range of 0.35 to 0.60;
the second ingredient encapsulated in the capsule assembly using the excipient to carry the second ingredient into the capsule assembly, wherein the second ingredient is therapeutic and non-homeopathic and the capsule assembly comprises the homeopathic carrier.

17. The article of manufacture of claim 16, wherein the excipient has a flowability index in the range of 80-90.

18. A method for encapsulating a homeopathic ingredient with a second ingredient, the method comprising:
preparing an excipient as a homeopathic carrier by diluting and succussing the homeopathic ingredient in a liquid diluent, applying the diluted homeopathic ingredient to the excipient, and drying the diluted homeopathic ingredient on the excipient; and
encapsulating the second ingredient using the excipient to carry the second ingredient into a capsule assembly, wherein the excipient is a glidant, the second ingredient is therapeutic and non-homeopathic, and the capsule assembly comprises the homeopathic carrier.

* * * * *